United States Patent
El-Baz et al.

(10) Patent No.: US 12,078,705 B2
(45) Date of Patent: *Sep. 3, 2024

(54) AUTOMATED SEGMENTATION OF TISSUE IN MAGNETIC RESONANCE IMAGING

(71) Applicant: University of Louisville Research Foundation, Inc., Louisville, KY (US)

(72) Inventors: Ayman S. El-Baz, Louisville, KY (US); Susan J. Harkema, Louisville, KY (US); Enrico Rejc, Louisville, KY (US); Ahmed Shalaby, Louisville, KY (US); Samineh Mesbah, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/323,564

(22) Filed: May 25, 2023

(65) Prior Publication Data

US 2023/0417851 A1 Dec. 28, 2023

Related U.S. Application Data

(63) Continuation of application No. 16/771,059, filed as application No. PCT/US2018/064760 on Dec. 10, 2018, now Pat. No. 11,675,039.

(60) Provisional application No. 62/596,941, filed on Dec. 11, 2017.

(51) Int. Cl.
*G01R 33/56* (2006.01)
*G01R 33/48* (2006.01)

(52) U.S. Cl.
CPC ..... *G01R 33/5608* (2013.01); *G01R 33/4828* (2013.01); *G01R 33/5607* (2013.01)

(58) Field of Classification Search
CPC ............ G01R 33/5608; G01R 33/4828; G01R 33/5607; G16H 30/40; G16H 50/50
USPC ........................................................ 600/410
See application file for complete search history.

(56) References Cited

U.S. PATENT DOCUMENTS

| | | | | |
|---|---|---|---|---|
| 8,175,349 | B2 * | 5/2012 | Jerebko | G06T 7/12 382/128 |
| 9,606,208 | B2 * | 3/2017 | Paul | G01R 33/5612 |
| 10,254,366 | B2 * | 4/2019 | Grodzki | G01R 33/543 |
| 2008/0044074 | A1 * | 2/2008 | Jerebko | G06T 7/12 382/128 |

OTHER PUBLICATIONS

Makrogiannis, Sokratis, et al. "Automated quantification of muscle and fat in the thigh from water-, fat-, and nonsuppressed MR images." Journal of Magnetic Resonance Imaging 35.5 (2012): 1152-1161. (Year: 2012).*

* cited by examiner

*Primary Examiner* — Christopher P McAndrew
(74) *Attorney, Agent, or Firm* — Dentons Bingham Greenebaum LLP; Brian W. Chellgren

(57) ABSTRACT

An automated segmentation system for medical imaging data segments data into muscle and fat volumes, and separates muscle volumes into discrete muscle group volumes using a plurality of models of the medical imaging data, and wherein the medical imaging data includes data from a plurality of imaging modalities.

21 Claims, 11 Drawing Sheets

(a)    (b)

AUTOMATED SEGMENTATION OF TISSUE IN MAGNETIC RESONANCE IMAGING

This application is a continuation of U.S. patent application Ser. No. 16/771,059, filed Jun. 9, 2020, which is the national stage entry of international application PCT/US2018/064760, filed Dec. 10, 2018, which claims the benefit of U.S. provisional patent application Ser. No. 62/596,941 filed Dec. 11, 2017, all of which are incorporated herein by reference.

FIELD OF THE INVENTION

An automated segmentation system for medical imaging data segments data into muscle and fat volumes, and separates muscle volumes into discrete muscle group volumes using a plurality of models of the medical imaging data, and wherein the medical imaging data includes data from a plurality of imaging modalities.

BACKGROUND OF THE INVENTION

This invention relates in general to methods for automatic muscle and fat volume segmentation in digital image files from magnetic resonance imaging. Severe spinal cord injury (SCI) leads to skeletal muscle atrophy and adipose tissue infiltration within the skeletal muscle and between muscles, which can result in compromised muscle mechanical output and lead to health-related complications, such as higher risk of diabetes, cardiovascular diseases and metabolic syndrome. However, in spite of the above-mentioned deleterious adaptations due to SCI, paralyzed skeletal muscles can be reconditioned by different treatments that include neuromuscular electrical stimulation, dietary programs and assisted movement training.

Magnetic resonance imaging (MRI) of thigh muscles is a commonly used technique to evaluate the effects of conditions such as ageing, obesity and SCIs on skeletal muscle mass and adipose tissue distribution. The volumetric thigh images that have been generated by 3D MRI are utilized to monitor the effectiveness of rehabilitation interventions and other treatments on reversing the negative physiological adaptations induced by these conditions on the skeletal muscle system. In order to find quantification measures for evaluation and comparison, the MRI volumes must first be segmented based on muscle tissue, subcutaneous fat and inter-muscular fat. It is also of importance to assess and compare the muscle mass of specific muscle groups or individual muscles.

The task of segmenting MR images into meaningful compartments has typically been done manually by experts. However, the manual methods have been suffering from inter- and intra-operator variability, being laborious and time-consuming and hence not being scalable to a higher number of patients and treatment methods. Therefore, reliable and accurate automatic or semi-automatic methods for detecting anatomical volumes of interest from MR images are highly needed and will offer reliability, repeatability and scalability in various medical applications.

Several automatic and semi-automatic methods have been proposed in the literature for segmentation of 2-D thigh MR images using intensity and shape-based methods. Positano et al. (Journal of Magnetic Resonance Imaging (29), 677-684 (2009)) used a fuzzy clustering technique and an active contour algorithm to segment the subcutaneous fat and bone in thigh MR images recorded from obese individuals. They also used an expectation maximization (EM) algorithm to segment the inter-muscular fat from soft tissue. In a similar study, Urricelqui et al. (International Journal of Medical, Health, Biomedical, Bioengineering and Pharmaceutical Engineering 3(10), 314-320 (2009)) used an intensity-based method with adaptive thresholding for segmenting bone, fat tissue and muscle tissue. Makrogiannis et al. (J. Magn. Reson. Imaging 35(5), 1152-1161 (2012)) used parametric deformable model to segment subcutaneous fat and central clustering technique to identify the inter-muscle fat from muscle tissue. An unsupervised multi-parametric k-means clustering method proposed in Valentinitsch et al. (J. Magn. Reson. Imaging 37(4), 917-927 (2013)) to segment intermuscular, subcutaneous fat and muscle tissue in patients with type 2 diabetes and in the control group. Moreover, Orgiu et al. (J. Magn. Reson. Imaging 43(3), 601-10 (2015)) used a fuzzy c-mean algorithm and Snake active contour model to distinguish between inter-muscular and subcutaneous fat in obese and elderly individuals.

All of these studies are focused on segmentation of fat and muscle area in 2-D images using intensity and shape-based methods only. Furthermore, no muscle group segmentation was done in these studies. There have been a number of studies done recently on muscle volume segmentation on 3-D MRI datasets of thigh muscles where the objective was to segment the entire volume of certain muscle groups or each individual muscle in addition to subcutaneous and inter-muscular fat segmentation. Baudin et al. (MICCAI, pp. 569-576 (2012)) presented a method for encoding shape models based on training dataset into a random walker segmentation framework to segment each individual muscle of the human thigh. In a similarly task, Andrews and Hamarneh (IEEE Transactions on Medical Imaging 34(9), 1773-1787 (2015)) proposed a probabilistic approach to build a statistical shape model using the principal component analysis to a set of M K-label manually generated training segmentations. Ahmad et al. (Proceedings of SPIE (2014)) proposed a combination framework of atlas construction and image registration to segment the quadriceps muscle group. However, no segmentation of adipose tissue was done in this study. Another atlas-based segmentation method was proposed by Troter et al. (J. of Magn. Reson. Mater. Phy. 29, 245-257 (2016)) to segment four individual muscle volumes inside the quadriceps group. They presented single-atlas and multiple-atlas approaches for the segmentation, suggested that the single-atlas method was more robust for single muscle segmentation and has a better accuracy. However, there is no utilization of any appearance features in their model and they only focused on young healthy male population which, as mentioned in Orgiu et al., some of the proposed automatic methods for segmentation might show poor accuracy in populations with medical conditions that negatively affect the muscle and fat infiltration areas. Furthermore, none of the aforementioned studies focused on using automatic segmentation methods on populations with severe SCI.

SUMMARY

Embodiments of the present invention relate to a new automatic technique for quantifying the negative effects of severe SCI on thigh muscles and fat distribution in humans. In individuals with SCI, the muscle paralyzed by an upper motor neuron lesion undergoes severe atrophy and consequently the reduction of force generation capability. These negative adaptations, among others, may limit motor functions even if neuronal control was sufficient. These individuals are also prone to gain adipose tissue at different sites (i.e. subcutaneous and inter-muscular fat), which can also lead to secondary complications such as higher risk of diabetes, cardiovascular diseases and metabolic syndrome. Presented herein is a computer-implemented approach to 1) automatically segment MRI volumes of adipose tissue into subcutaneous and inter-muscular fat using an intensity-based approach; 2) segment the MRI volumes related to the thigh muscle tissue into three main muscle groups: knee extensors, knee flexors and hip adductor muscles using the joint Markov Gibbs Random Field (MGRF) model. The main motivation behind developing the joint MGRF model is to use intensity, spatial and shape concurrently to overcome intensity-based variations, handle the intra-/inter-muscle inhomogeneity and define muscle compartments, respectively. While this computer-based approach is discussed primarily in terms of segmentation of MRI volumes in thigh muscle tissue and adipose tissue, the computer-implemented algorithms and equations disclosed herein may also be used to segment other muscle tissues upon construction of suitable atlases (prior shape information) using a sufficient number of training volumes.

The automatic framework proposed herein has been found to precisely segment thigh muscle groups and fat volumes in healthy and SCI individuals with total accuracy of 94.76±1.70 for muscle group segmentation and 96.86±3.48 for total fat segmentation. The high accuracy presented herein for muscle group segmentation demonstrates the advantage of incorporating appearance and spatial information into a level-set model for automatic muscle volume segmentation. While this disclosure focuses primarily on SCI subjects, the close accuracy in the ND group indicates that this framework has the capacity to be applied in broad population where the segmentation of thigh muscle and fat volumes can be a valuable assessment. The framework is able to accurately segment and compartmentalize muscle and adipose tissue, and detect changes within a compartment. In this case, it was able to demonstrate an increase in inter-muscular fat relative to muscle volume in patients with SCI. There is a promise that this methodology could have broad application in detecting, and tracking over time, muscle atrophy in patients with loss of mobility and muscle mass gain due to rehabilitative interventions.

One advantage of this framework over other automatic and semi-automatic methods of segmentation of thigh MR images is that, in addition to adaptive prior shape information, two other image features (first order appearance and spatial interactions) are incorporated into the level-set segmentation. These features are estimated directly from the input data to be segmented, making the proposed framework an adaptive approach.

This summary is provided to introduce a selection of the concepts that are described in further detail in the detailed description and drawings contained herein. This summary is not intended to identify any primary or essential features of the claimed subject matter. Some or all of the described features may be present in the corresponding independent or dependent claims, but should not be construed to be a limitation unless expressly recited in a particular claim. Each embodiment described herein is not necessarily intended to address every object described herein, and each embodiment does not necessarily include each feature described. Other forms, embodiments, objects, advantages, benefits, features, and aspects of the present invention will become apparent to one of skill in the art from the detailed description and drawings contained herein. Moreover, the various apparatuses and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

A better understanding of the present invention will be had upon reference to the following description in conjunction with the accompanying drawings.

DETAILED DESCRIPTION OF THE PREFERRED EMBODIMENTS

Figure 1:
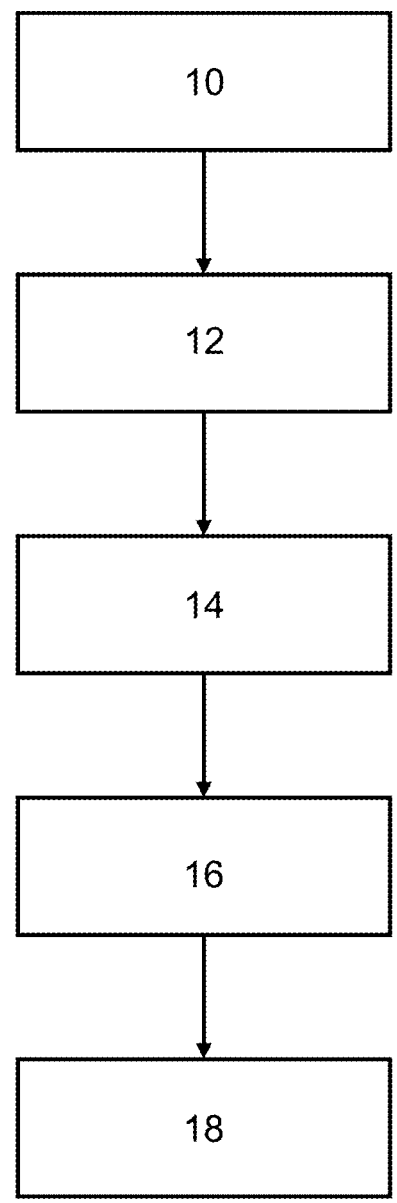
FIG. 1 depicts a flowchart of the process for segmentation and quantification of muscle and adipose tissue in MRI image data.

For the purposes of promoting an understanding of the principles of the invention, reference will now be made to selected embodiments illustrated in the drawings and specific language will be used to describe the same. It will nevertheless be understood that no limitation of the scope of the invention is thereby intended; any alterations and further modifications of the described or illustrated embodiments, and any further applications of the principles of the invention as illustrated herein are contemplated as would normally occur to one skilled in the art to which the invention relates. At least one embodiment of the invention is shown in great detail, although it will be apparent to those skilled in the relevant art that some features or some combinations of features may not be shown for the sake of clarity.

Any reference to "invention" within this document is a reference to an embodiment of a family of inventions, with no single embodiment including features that are necessarily included in all embodiments, unless otherwise stated. Furthermore, although there may be references to "advantages" provided by some embodiments of the present invention, other embodiments may not include those same advantages, or may include different advantages. Any advantages described herein are not to be construed as limiting to any of the claims.

Specific quantities (spatial dimensions, dimensionless parameters, etc.) may be used explicitly or implicitly herein, such specific quantities are presented as examples only and are approximate values unless otherwise indicated. Discussions pertaining to specific compositions of matter, if present, are presented as examples only and do not limit the applicability of other compositions of matter, especially other compositions of matter with similar properties, unless otherwise indicated. The terms "fat" and "adipose" are used interchangeably.

With respect to the system and methods disclosed herein, let $R=\{(x,y,z): 0 \leq x \leq X-1, 0 \leq y \leq Y-1, 0 \leq Z \leq Z-1\}$; $Q=\{0, 1, \ldots, Q-1\}$; and $L=\{0, 1, 2, 3\}$ denote a finite 3-D arithmetic lattice of the size of XYZ supporting grayscale images and their region (segmentation) maps, a finite set of Q integer gray values, and a set of region labels, respectively. Let $g=\{g_{x,y,z}: (x,y,z) \in R; g_{x,y,z} \in Q\}$ and $m=\{m_{x,y,z}: (x,y,z) \in R; m_{x,y,z} \in L\}$ be a grayscale image taking values from Q, i.e., $g: R \to Q$, and a region map taking values from L, i.e., $m: R \to L$, respectively.

A 3-D probabilistic based process 10 for fat suppressed (FS) and water suppressed (WS) MRI muscles and fat segmentation is displayed as FIG. 1. The process 10 broadly comprises a preprocessing step 12 to prepare input MRI images for automatic segmentation, which includes bias-field correction, extraction of the central fifty slices between greater trochanter and lateral epicondyle of the femur, and cropping and resizing the MRI images to include only one thigh for further processing steps. Bias-field correction, cropping and resizing images are techniques commonly known in the art. Subsequent to the preprocessing step 12, automatic segmentation of MRI images is divided into four sequential steps. In first step 14, the sum of WS and FS volumetric MRI is utilized to obtain the mask of the whole thigh volume utilizing Linear Combination of Discrete Gaussians (LCDG) algorithm. The same method was used on each FS-MRI volume to initially extract muscle volume and WS-MRI volume is used to segment the total adipose tissue. Moreover, the subcutaneous adipose tissue (SAT) was separated from the inter-muscular adipose tissue (IMAT) by overlaying the muscle tissue mask, obtained from the FS volume, on the total fat segmentation. In second step 16, each segmented muscle volume and its manually segmented muscle groups (training dataset) is co-aligned to a reference dataset using a 3-D cubic B-splines-based approach (described in Glocker et al. (Annual Review of Biomedical Engineering 13, 219-244 (2011))) to account for the anatomical differences of each patient's extracted muscle volumes from adipose tissue and bone. In third step 18, a joint MGRF model is implemented that simultaneously maximizes the likelihood estimation of three components: Appearance-based shape (muscles anatomy), spatial (second order appearance) and intensity (first order appearance) model by using iterated conditional modes (ICM) to localize and segment three muscle groups (knee extensors, knee flexors and the medial compartment, which includes Sartorius, adductor longus, gracilis, adductor brevus, and adductor magnus muscles) in the MRI images. In fourth step 20, the volumes of the segmented tissues are calculated to quantify the effects of SCI on human thigh muscles.

Figure 2:
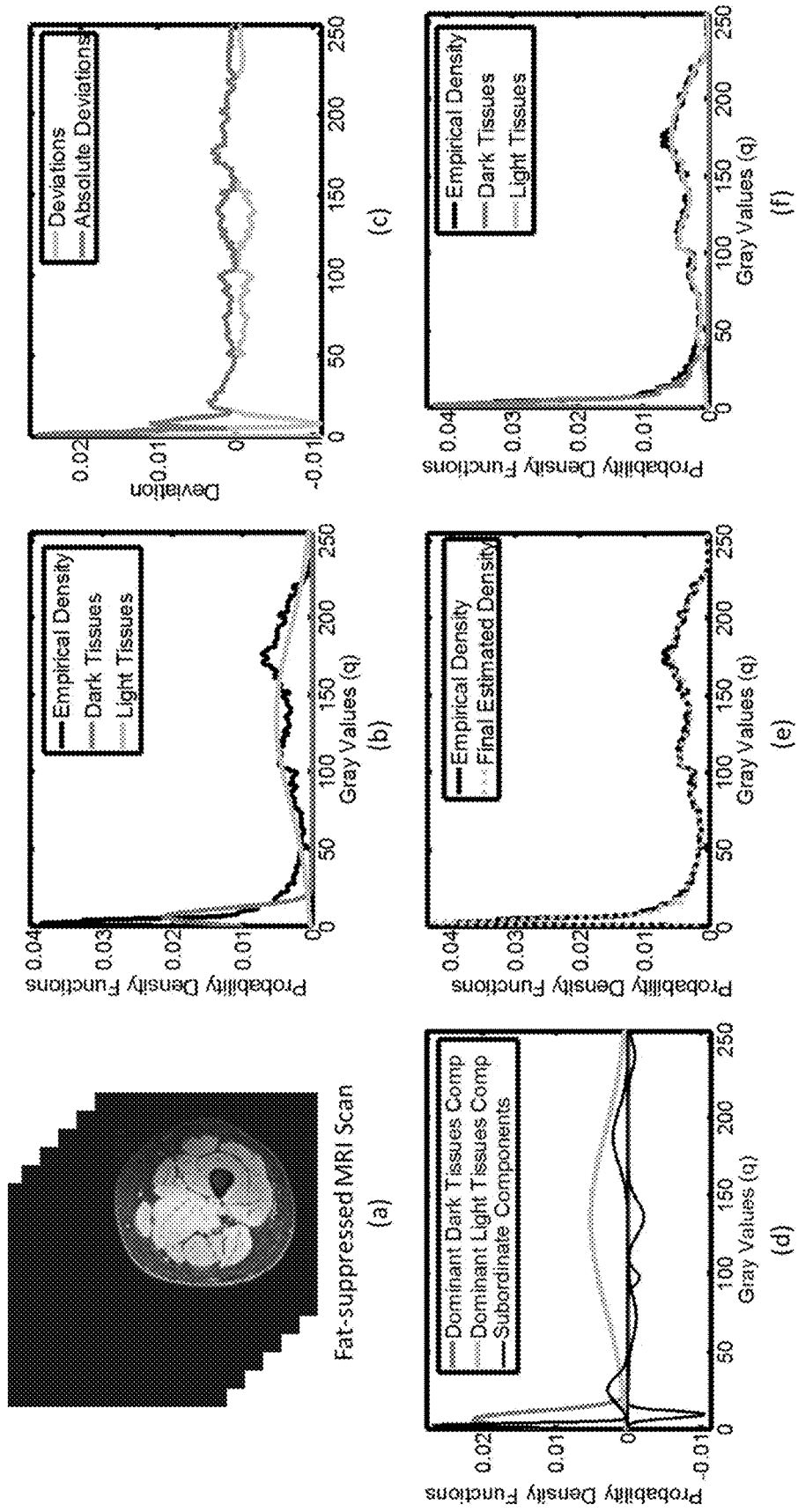
FIG. 2A depicts exemplary 3D FS-MRI image data.
FIG. 2B is a chart of probability density functions vs. gray values of voxels the image data in FIG. 2A, as determined empirically, and as approximated via LCDG using two dominant Discrete Gaussians.
FIG. 2C is a chart depicting the deviations (standard and absolute) between the empirical and estimated probability density functions in FIG. 2B.
FIG. 2D is a chart depicting LCDG algorithm output on the dominant and subordinate DGs in the image data in FIG. 2A.
FIG. 2E is a of probability density functions vs. gray values of voxels the image data in FIG. 2A, as determined empirically and the final estimate determined by LCDG algorithm.
FIG. 2F is a chart depicting the final estimate determined by LCDG algorithm, and the individual Discrete Gaussians segmenting dark tissue and light tissue

With respect to the first step 14, LCDG is used to find the threshold for each gray volume that extracts the two classes (corresponding to the dark tissues and light tissues) from their background. In case of FS-MRI scans, as shown in FIG. 2A, adipose tissue is dark and muscle tissue is light (vice versa for WS-MRI scans). At the end of the first step 14, two probabilities are generated for each voxel of the input volumes: P1, which is the probability of the voxel to belong to class 1 (dark tissue), and P2, which is the probability of the voxel to belong to class 2 (light tissue). The voxel-wise LCDG probability is combined to obtain the muscle, SAT and IMAT areas from FS, WS and FS+WS MRI scans. Due to the opposite contrasts for adipose and muscle tissues in FS and WS images, the whole adipose tissue can be segmented in WS images and the whole muscle area segmented in FS images using LCDG alone, and the segmented muscle area as a mask to separate SAT from IMAT.

FIGS. 2A-F illustrate exemplary steps of muscle area segmentation using LCDG algorithm for FS-MRI volumes. FIG. 2A depicts input FS-MRI image data. FIG. 2B depicts the initial approximation of the bi-modal empirical distribution of Q=256 grey levels over a typical FS-MRI volume of human thigh. The dominant modes represent the brighter muscles area and its darker background, respectively. After the additive and subtractive parts of the absolute deviation are approximated with the Discrete Gaussian (DG) mixtures, the initial mixed LCDG-model consists of the 2 dominant, 4 additive (blue curves), and 4 subtractive DGs (brown curves), as shown in shown in FIGS. 2C and 2D. Finally, the estimated LCDG as well as conditional LCDG models of the two classes (i.e. muscles and adipose tissues) are illustrated in FIGS. 2E and 2F. This algorithm is also used for WS-MRI scans to segment the fat tissue and FS+WS to segment the whole thigh area and the bone.

Joint Markov Gibbs Random Field Model

In order to divide the extracted muscles area into various groups in the third step 18, a registered-to-reference database of grayscale volume, g, of the muscles area and its map, m, are described with a joint probability model: P(g,m)=P(g|m) P(m), which combines a conditional distribution of the input volume given the map P(g|m), and an unconditional probability distribution of maps P(m)=$P_{sp}$(m) Pv(m), where, $P_{sp}$(m) represents an adaptive shape prior. Pv(m) is a Gibbs probability distribution with potentials V, which denotes a sample of a 3D MGRF model of m.

1. Appearance-Based Shape Model

In order to reduce the variability across subjects and enhance the segmentation accuracy, an adaptive shape model of each muscle group is employed. To create the shape database, a training set of volumes, collected from different subjects, are registered to a reference dataset in second step 16 using a 3-D B-splines-based transformation developed in Glocker et al. The selection for training dataset has been done based on the 2-D correlation coefficient (a number between 0 and 1) between the grayscale images of the manually segmented volumes and the test slices from the subject. If the average correlation coefficient for the whole volume is more than or equal to 0.5, that dataset will be selected for training otherwise it will be rejected. After selection, the training volumes are registered to the test volume. Therefore, for each new test subject, an individual training set is built to reduce variability in muscle group segmentation.

Each source volume f (i.e., each of the training subjects) is aligned to the target volume, or reference template g on a domain $Q \subset R^3$ by using a non-rigid registration. Given a certain source f, the registration estimates the deformation field T for all $x \in \Omega$, by displacing a sparse grid, $\Omega' \subset \Omega$ of control points, $\zeta$:

$$T(x)=x+\Sigma_{\zeta \in \Omega'} \zeta((\|x-\zeta\|)\Delta \zeta \quad (1)$$

where $\Delta\zeta$ is the displacement vector of the control point $\zeta$ and the weighting function $\zeta(.)$ measures the contribution of any control point in $\Omega'$ to the displacement of a point in $\Omega$. The goal deformation field minimizes the point-wise dissimilarity between the target g and the deformed source f:

$$E(T) = \frac{1}{|\Omega'|} + \sum_{\zeta \in \Omega'} \frac{\phi(g(x), f(T(x)))}{\zeta(\|x-\zeta\|)} dx \quad (2)$$

where $\phi$ is the dissimilarity function (we used the sum of absolute differences). The objective function in Eq. (2) is minimized using a Markov random field model of displacements of the control points $\zeta$. The dense displacement field is then determined from the control point displacements through representing free form deformations (FFDs) via cubic B-splines.

The probabilistic shape priors are spatially variant independent random fields of region labels, as follows:

$$P_{sp}(m)=\Pi p_{sp:x,y,z}(m_{x,y,z}) \quad (3)$$

where Psp:x,y,z(l) is the voxel-wise empirical probabilities for each label $l \in L$. To segment each input MRI data, an adaptive process guided by the visual appearance features of the input MRI data is used to construct the shape prior. This shape prior consists of four labels: the 3 muscle groups and the background. In the training phase, N−1 (N number of subjects) data sets manually segmented by an MRI expert are used to create the probabilistic maps for the four labels. For the testing phase, each test MRI volume is registered using the same approach in Glocker et al., to the training sets used to create the discussed shape prior.

2. Spatial Interaction or Second-Order Appearance Model

In order to overcome noise effects and to ensure segmentation homogeneity, spatially homogeneous 3D pair-wise interactions between the region labels are additionally incorporated in the proposed segmentation model. These interactions are estimated using the Potts model, i.e., an MGRF with the nearest 26-neighbors of the voxels (also known as cliques), and analytic bi-valued Gibbs potentials, that depend only on whether the nearest pairs of labels are equal or not. The utilized second-order 3D MGRF model of the region map m is defined as:

$$P_V(m) = \frac{1}{Z_{v_s}} \exp \sum_{(x,y,z) \in R} \sum_{(x',y',z') \in v_s} V(m_{x,y,z}, m_{x+x',y+y',z+z'}), \quad (4)$$

where $Z_{v_s}$ is the normalization factor. Let $f_{eq}(m)$ denote the relative frequency of equal labels in the neighboring voxel pairs. The initial region map results in an approximation with the following analytical maximum likelihood estimates of the potentials:

$$v_{eq}=-v_{ne} \approx 2f_{eq}(m)-1, \quad (5)$$

which allows for computing the voxel-wise probabilities $p_{V:x,y,z}(l)$ of each label; $l \in L$.

3. Intensity or First-Order Appearance Model

The disclosed approach also accounts for the visual appearance of the muscles besides the learned shape model and the spatial interactions. Therefore, an intensity-based model using LCDG with positive and negative components, is applied to increase the initially obtained accuracy. Given that the three muscle groups (i.e., knee extensors, knee flexors and the medial compartment) have different adipose tissue distributions, the LCDG presents an accurate model of the empirical density of the gray level in each initially segmented muscle group. Each voxel in the FS-MRI image has a gray value and by using the three models built by LCDG, three probability densities can be calculated for that voxel. The algorithm assigns that voxel to the class (muscle group) that has the highest probability density (occurrence). Put another way, the appearance model uses the LCDG method to approximate the empirical density of each initially segmented muscle group using a combination of DGs. The goal of using LCDG model here is to approximate three probability density models for the gray values within each muscle compartment. Since each voxel has a gray value, the density of this gray value can be estimated using the three LCDG models and assign that voxel to a class (muscle group) with highest density (occurrence).

The muscle group segmentation procedure is summarized in Algorithm 1 below.

Algorithm 1
  1. Build our shape prior from the training atlas.
  2. For each input FS and WS MRI volume with grayscale volume g:
      a. Use LCDG to initially extract muscle volume from adipose tissue and bone.
      b. Select atlas volumes using 2-D correlation coefficient measure between the training database and the target volume.
      c. Use non-linear registration to transpose selected atlas volumes' voxels to the target volume space.

d. Form an initial region map m using the marginal estimated density and prior shape of each muscle group label.
e. Find the Gibbs potentials for the MGRF model from the initial map.
f. Approximate the marginal intensity distribution P(g|m) of each muscle group using LCDG.
g. Improve the region map m by assigning each voxel to a class with the highest probability density based on its gray value.

First Set of Experimental Results

The 3-D MRI slices were recorded using Siemens 3T Magnetom Skyra with pulse sequence—t1 vibe (for 3-D VIBE images) for in phase, opposite phase, water, and fat imaging. The volume dimensions (X, Z, Y) are 320×320× 208 and the series length is 1. Voxel dimensions (X, Z, Y) are 1.5×1.5×1.5 mm, size of series point is 0.006 seconds and the slice gap is equal to zero. The thigh MRI scans analyzed in this study (N=20) were collected from 10 male individuals with chronic motor complete SCI (age: 34.4±9.0 years; time since injury: 7.3±8.9 years; 7 of them with American Spinal Injury Association Impairment Scale (ASIA) score A, 2 with score B and 1 with score C) and 10 healthy male non-disabled subjects (age 28.7±3.8).

The 50 central MRI slices between greater trochanter and lateral epicondyle of the femur were considered for further analysis, although in other embodiments, the number of analyzed thigh MRI slices may be increased from 50 to the entire thigh, or an intermediate between the two. All manual segmentations used in training and verifying the segmentation results were created and revised by MRI experts using MANGO software.

Figure 3:
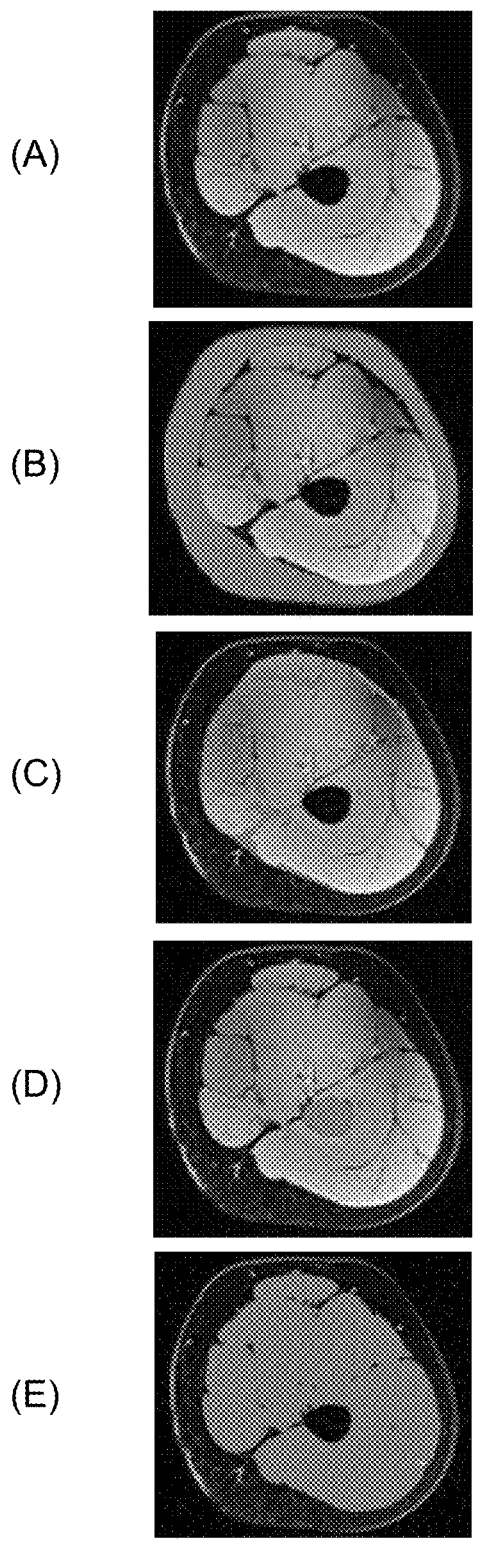
FIG. 3 depicts the application of LCDG algorithm to segment soft tissue: (A) original image, (B) image with highlighted subcutaneous adipose tissue, (C) image with highlighted intermuscular adipose tissue, (D) image with highlighted bone, (E) image with highlighted muscle tissue.
Figure 4:
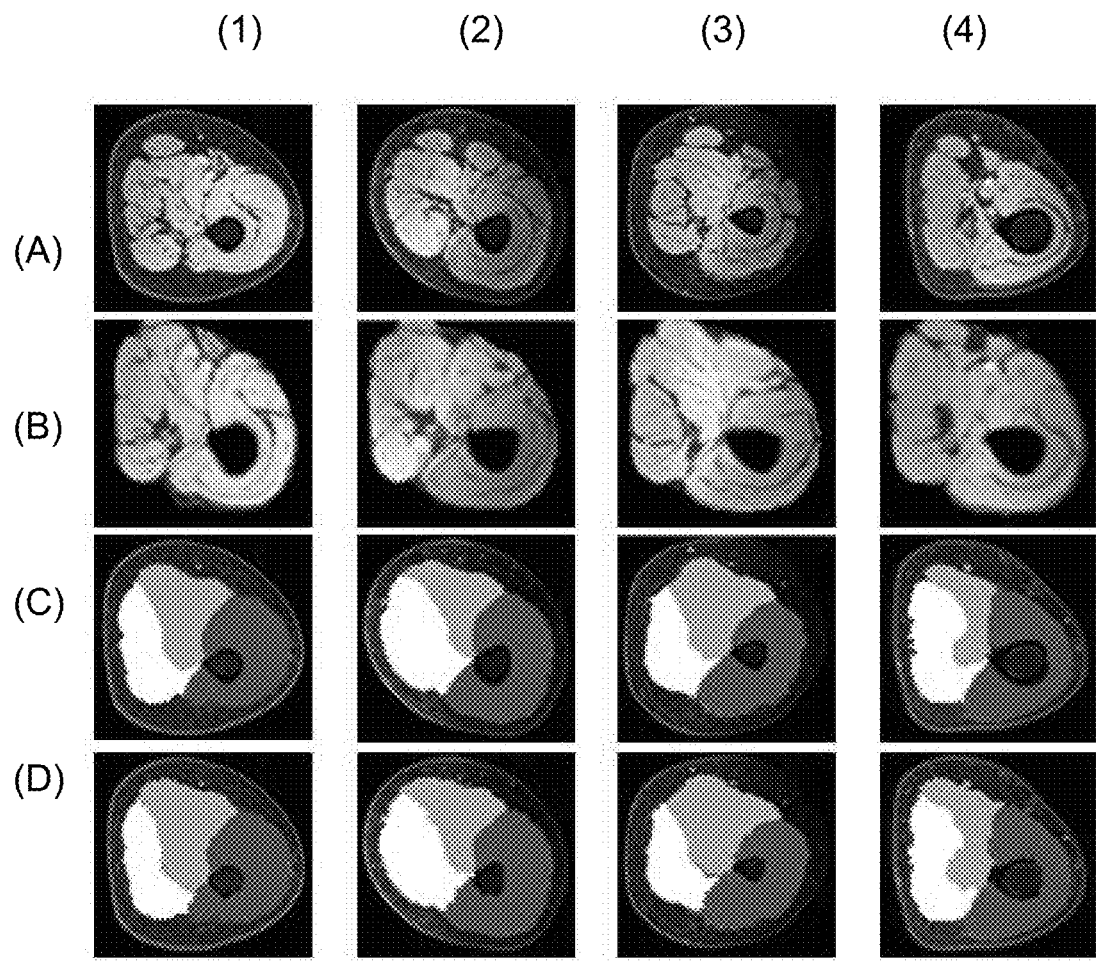
FIG. 4 depicts four examples (columns 1, 2, 3, and 4) of muscle group segmentation algorithm: (row A) original images, (row B) registration to the reference atlas, (row C) manually segmented muscle groups, and (row D) automatic segmentation of muscle groups.

FIG. 3 shows an example of the LCDG results on the FS- and WS-MRI volumes for extraction of the whole muscle area, bone, and segmenting the subcutaneous fat from the inter-muscular fat. In FIG. 4, the three steps for muscle groups segmentation is presented for four sample MR images.

The accuracy of the initial segmentation of fat tissue was tested by comparison of the automatic results with the manual segmentation of subcutaneous and inter-muscular fat. The comparison was made based on calculating the Dice similarity coefficient (DSC) as the similarity measure. To obtain the accuracy for automatic muscle groups segmentation, we used the common technique of leave-one-subject-out, where N−1 subjects are used to build the atlas and one subject was left out for testing, and repeat this for all subjects for SCI and ND groups separately. The results for accuracy measures are presented in Table 1.

Figure 5:
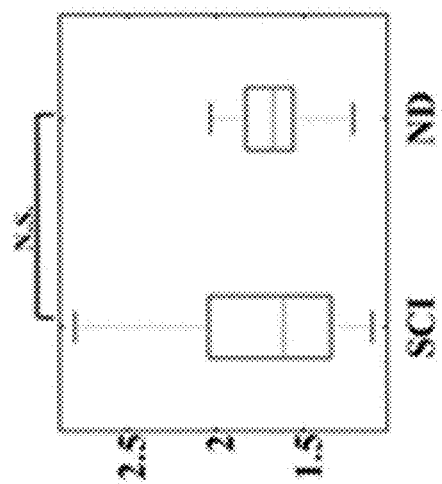
FIG. 5 depicts boxplot representations of calculated ratios for individuals with SCI and non-disabled (ND) individuals: (A) subcutaneous volume/muscle volume, (B) inter-muscular volume/muscle volume, and (C) extensor volume/flexor volume.
Figure 5:
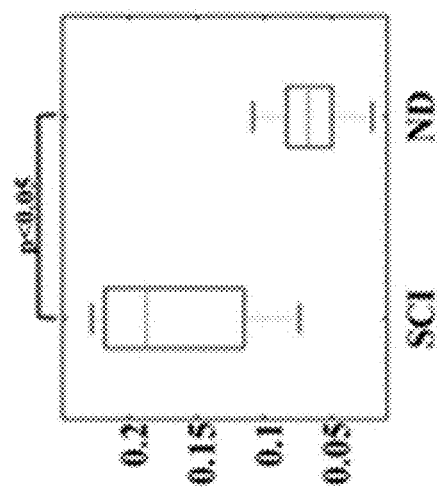
Figure 5:
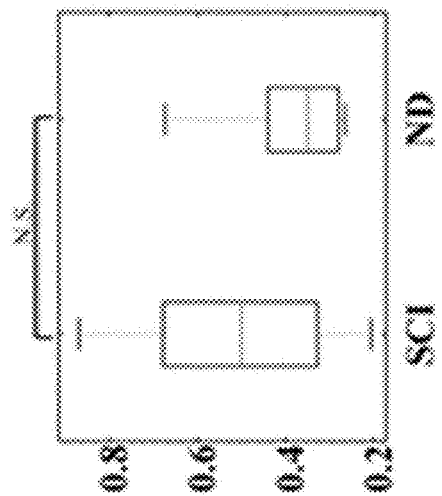
Figure 6:
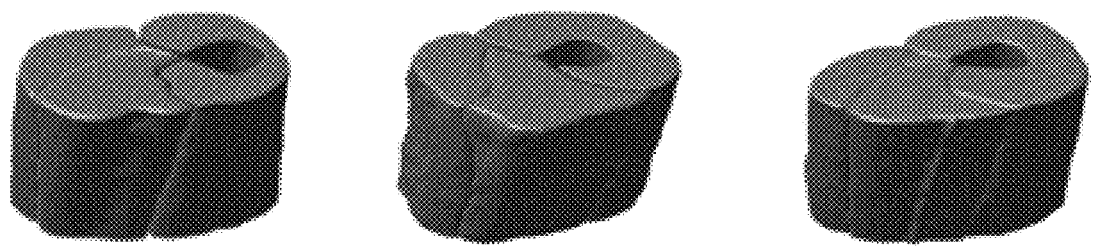
FIG. 6 depicts 3-D reconstructions of muscle group segmentations for three subjects using the methods of the present invention.

The three ratios based on the volumes of the subcutaneous fat to muscle tissue, inter-muscular fat to muscle and extensor to flexor for all subjects in SCI and ND groups were calculated, as shown in FIG. 5. In order to see if there is a statistically significant difference between SCI and ND groups, we used the non-parametric Mann-Whitney test on the three ratios and results show that the inter-muscular fat to muscle volume shows significant difference between the two groups (2-tailed p=0.001). 3-D reconstructions of the three segmented groups for different subjects are presented in FIG. 6. The disclosed segmentation technique is clearly successful in segmenting the three main muscle groups.

To evaluate the accuracy of fat segmentation results, the percentage of DSC was calculated by comparing the results of automatic segmentation to the ground truth for each subject. For evaluating the muscle group segmentation, the model was trained with N−1 subjects and tested on the remaining 1 subject, and repeated of every subject in SCI and non-disabled groups separately. The results were compared to the ground truth using DSC measure. Table 2 summarizes the average segmentation accuracy for each test subject. The proposed method reaches 96.71±1.55% overall DSC for muscle group segmentation, 94.02±2.16% for subcutaneous fat segmentation and 80.19±5.39% for intermuscular fat segmentation.

TABLE 2

The segmentation accuracy of the proposed approach for 10 SCI and 5 Non-disabled subjects

| Subject ID | Dice Similarity (%) | | | | |
|---|---|---|---|---|---|
| | Knee extensors | Knee flexors | Adduct muscles | Subcutaneous fat | Inter/Intra fat |
| SCI #1 | 98.66 | 96.84 | 96.68 | 91.00 | 72.69 |
| SCI #2 | 98.71 | 96.94 | 96.11 | 93.57 | 83.49 |
| SCI #3 | 98.73 | 96.91 | 96.49 | 93.25 | 82.34 |
| SCI #4 | 98.48 | 96.67 | 95.75 | 91.42 | 81.69 |
| SCI #5 | 98.29 | 96.94 | 96.82 | 91.53 | 83.59 |
| SCI #6 | 98.58 | 97.46 | 96.61 | 95.99 | 83.51 |
| SCI #7 | 98.04 | 96.30 | 95.53 | 96.87 | 83.10 |
| SCI #8 | 98.24 | 96.94 | 95.79 | 96.99 | 78.20 |
| SCI #9 | 98.70 | 97.22 | 96.61 | 94.89 | 84.40 |
| SCI #10 | 97.94 | 96.43 | 95.63 | 94.14 | 67.02 |
| ND #1 | 97.54 | 92.90 | 94.53 | 94.65 | 85.84 |
| ND #2 | 96.27 | 93.46 | 97.15 | 92.61 | 78.61 |
| ND #3 | 96.66 | 91.51 | 94.33 | 91.49 | 85.16 |
| ND #4 | 98.03 | 96.25 | 96.91 | 94.40 | 73.30 |
| ND #5 | 98.65 | 96.23 | 96.61 | 97.54 | 79.83 |

TABLE 1

The accuracy measure (percentage of DSC) of the proposed approach for 10 SCIs and 10 NDs

| | 1 | 2 | 3 | 4 | 5 | 6 | 7 | 8 | 9 | 10 |
|---|---|---|---|---|---|---|---|---|---|---|
| | SCI IDs | | | | | | | | | |
| Muscle group segmentation | 93.56 | 91.17 | 94.50 | 93.69 | 93.99 | 94.24 | 95.01 | 91.10 | 93.64 | 94.53 |
| Total fat segmentation | 98.30 | 94.84 | 99.69 | 99.58 | 95.78 | 98.77 | 93.20 | 86.34 | 93.95 | 95.38 |
| | ND IDs | | | | | | | | | |
| Muscle group segmentation | 96.52 | 95.26 | 96.54 | 96.46 | 96.42 | 94.68 | 95.62 | 94.16 | 97.06 | 97.16 |
| Total fat segmentation | 98.71 | 95.97 | 98.34 | 98.75 | 99.94 | 99.60 | 99.68 | 98.43 | 92.07 | 99.81 |

Second Set of Experimental Results

The 3-D MRI slices were recorded using Siemens 3T Magnetom Skyra with pulse sequence–t1 vibe (for 3-D VIBE images) for in phase, opposite phase, water, and fat imaging. The volume dimensions (X, Z, Y) are 320×320× 208 and the series length is 1. Voxel dimensions (X, Z, Y) are 1.5×1.5×1.5 mm, size of series point is 0.006 seconds and the slice gap is equal to zero. The thigh MRI scans analyzed in this study were collected from a total of 30 subjects. The characteristics of the 16 individuals with severe chronic SCI were the following: age (year): 32.4±9.1; time since injury (year): 6.7±7.7; 13 males and 3 females; 10 individuals classified as ASIA impairment scale (AIS) A, 5 individuals as AIS B, and 1 individual as C as for the International Standards for Neurological Classification of Spinal Cord Injury (31); height (m): 1.78±0.09; weight (kg): 77.19±12.48; body mass index (BMI) (kg/m2): 24.36±3.99. The 14 ND subjects included in this study presented were 11 males and 3 females with age (year): 28.47±3.8; height (m): 1.80±0.10; weight (kg): 92.56±15.30; BMI (kg/m$^2$): 28.54±4.27.

To evaluate the results we calculated the percentage segmentation accuracy from the ground truth (obtained from manual segmentation) using the Dice's coefficient (DC, equivalent to DSC, used above), $$\text{Recall}\left(R = \frac{TP}{TP+FN}\right),$$

Figure 7:
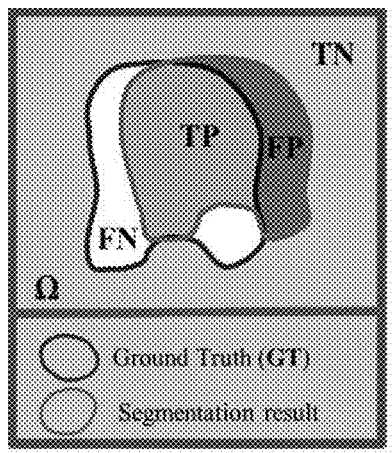
FIG. 7A depicts an exemplary overlay of a segmentation result atop a ground truth shape, displaying true positive (TP), false positive (FP), true negative (TN), and false negative (FN) regions.
FIG. 7B depicts calculations of Hausdorff distance between line X and line Y.
Figure 7:
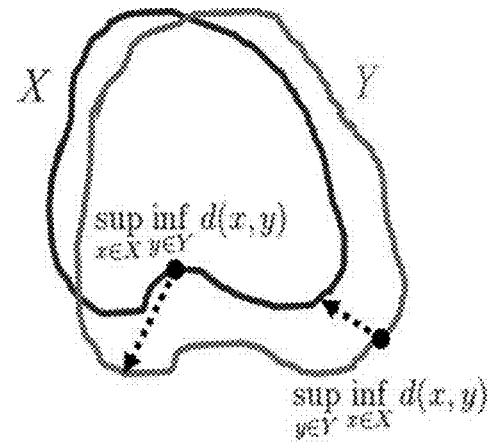

Precision $$\left(P = \frac{TP}{TP+FN}\right)$$

and the Hausdorff distance (HD). The DC measures the concordance between two enclosed volumes as follows $$DC\% = 100\frac{2TP}{FP+2TP+FN}, \quad (6)$$

where FP represents the number of false positive (i.e. the total number of the misclassified voxels of the background), FN is the number of false negative (i.e. the total number of the misclassified voxels of the object), and TP is the true positive (i.e. total number of the correctly classified pixels), as shown in FIG. 7A. On the other hand, The HD is defined as:

$$HD(X,Y) = \max\{\sup_{x \in X}\inf_{y \in Y} d(x,y), \sup_{y \in Y}\inf_{x \in X} d(x,y)\} \quad (7)$$

where X and Y are the boundaries of two different volumes. It measures how far two subsets of a metric space are from each other, as shown in FIG. 7B. High DC, R, and P and a low HD are desirable for good segmentation.

Manual Segmentation

Manual segmentation of MR images were performed by one expert operator using MANGO software (Research Imaging Institute, UTHSCSA) for determining SAT, IMAT, whole muscle, and the 3 muscle compartments considered herein.

Segmentation of SAT, IMAT and Bone

Figure 8:
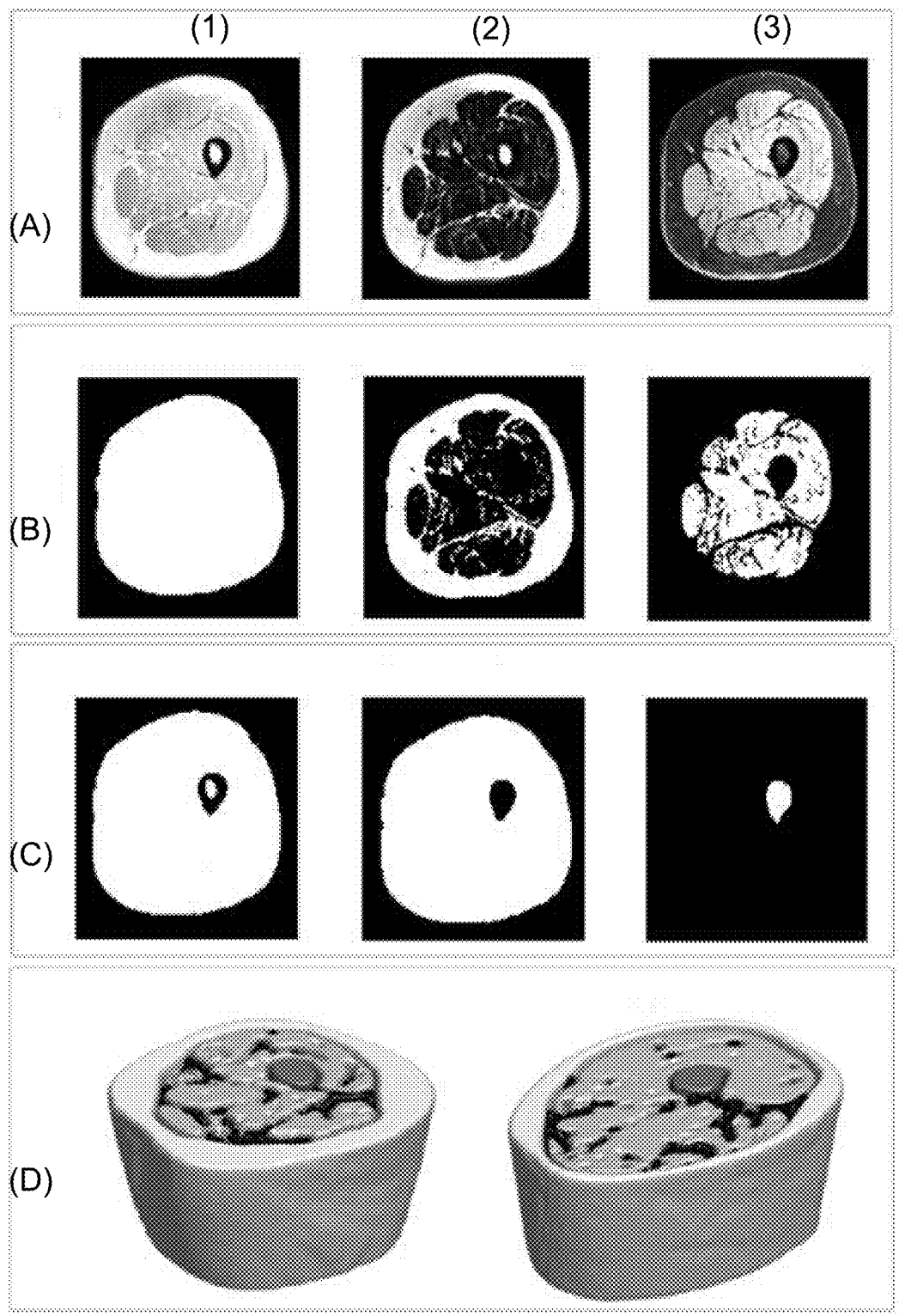
FIG. 8 depicts (row A) greyscale images of (column 1) FS+WS MRI scan, (column 2) WS MRI scan, (column 3) FS MRI scan, (row B) auto segmented binary mask of (column 1) thigh, (column 2) adipose tissue, (column 3) muscle tissue, (row C) automated segmentation of bone, highlighting (column 1) bone and bone marrow, (column 2) thigh mask without bone, (column 3) bone alone, and (row D) 3-D visualizations of (left) segmented thigh of SCI subject, and (right) segmented thigh of ND subject.

FIG. 8 shows examples of the LCDG results on the sum of WS- and FS-MRI volumes, WS-MRI volumes and FS-MRI volumes (FIG. 8A) for extraction of the whole thigh, whole fat, whole muscle mask (FIG. 8B) as well as bone area (FIG. 8C). Also, an example of 3D visualization of the final thigh segmentation results for SCI and ND is reported in FIG. 8D. The SAT and IMAT areas were separated by using the whole muscle area as a mask on the whole fat area as described above.

The average accuracy of the initial segmentation of fat tissue was tested by comparison of the automatic results with the manual segmentation of SAT, IMAT and thigh muscle. The comparison was made based on calculating the DC, R and P as accuracy measures. The average values of these three accuracy measures are presented in Table 3.

TABLE 3

The average (± SD) accuracy measures (Dice's coefficient (DC), Recall (R), and Precision (P) of the disclosed fat segmentation approach for SCI (N = 16) and ND (N = 14) individuals.

| | SCI | | | | ND | | |
|---|---|---|---|---|---|---|---|
| Avg. Metrics | SAT | IMAT | Thigh Muscle | Avg. Metrics | SAT | IMAT | Thigh Muscle |
| DC | 0.91 ± 0.06 | 0.85 ± 0.06 | 0.97 ± 0.02 | DC | 0.97 ± 0.01 | 0.86 ± 0.07 | 0.98 ± 0.01 |
| P | 0.94 ± 0.03 | 0.86 ± 0.09 | 0.98 ± 0.02 | P | 0.96 ± 0.02 | 0.82 ± 0.11 | 1.00 ± 0.00 |
| R | 0.89 ± 0.09 | 0.86 ± 0.10 | 0.96 ± 0.03 | R | 0.98 ± 0.01 | 0.91 ± 0.06 | 0.97 ± 0.03 |

Muscle Group Segmentation

Figure 9:
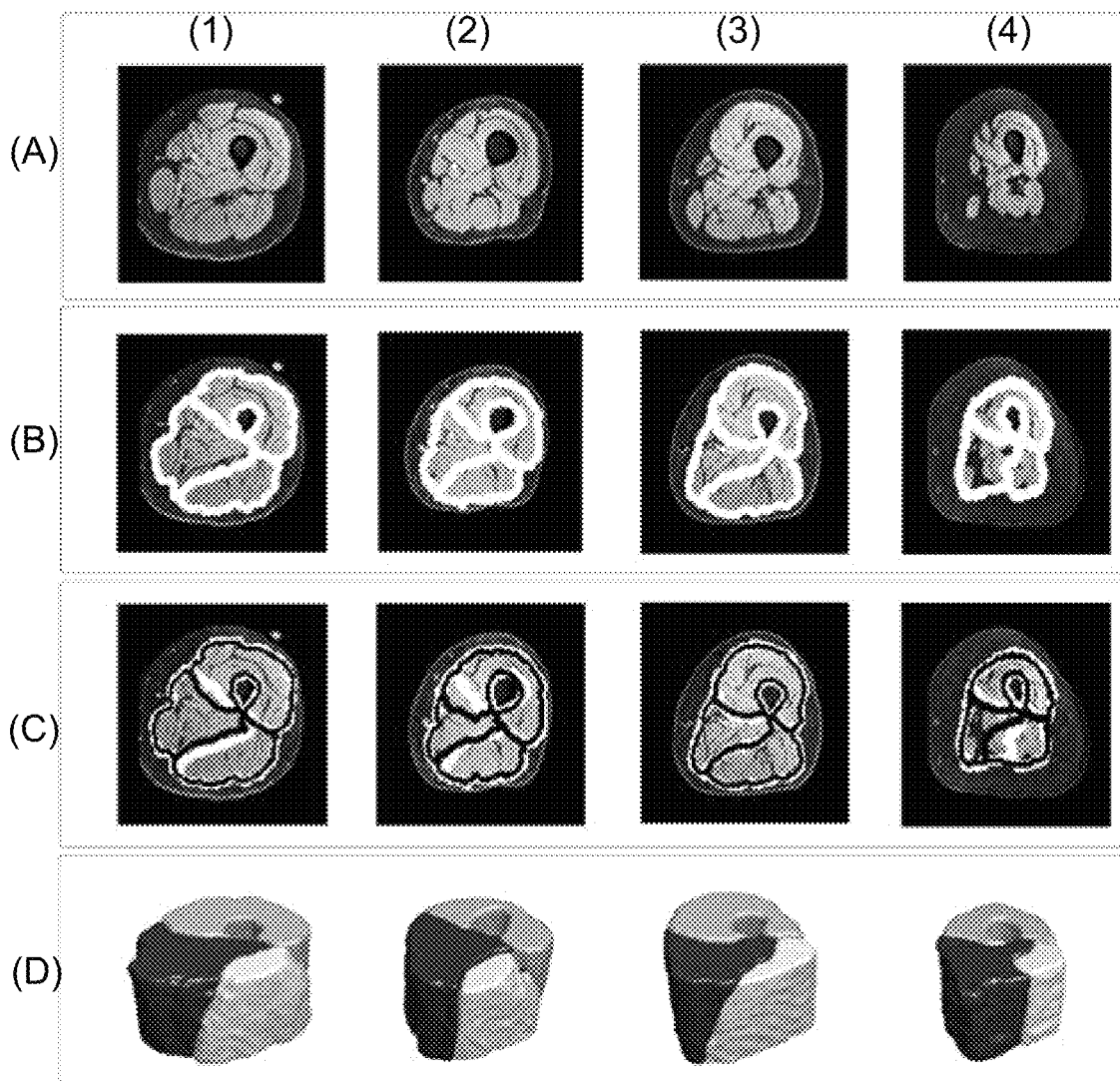
FIG. 9 depicts four examples (columns 1, 2, 3, and 4) of muscle group segmentation algorithm of SCI subjects: (row A) original images, (row B) automatic segmentation of muscle groups, (row C) manually segmented muscle groups overlaid on automatically segmented muscle groups, and (row D) 3-D visualizations of the segmented muscle groups.

To obtain the accuracy of the three automatic muscle group segmentations, the common technique of leave-one-subject-out was used, where N−1 subjects are used to build the atlas and one subject was left out for testing, and we repeated this for all subjects in the SCI and ND groups separately. FIG. 9 reports examples of the cross sectional area of the original grayscale MRIs (FIG. 9A), the results of the automatic segmentation of the muscle groups (FIG. 9B), manually segmented muscle groups overlaid on automatic segmentation (FIG. 9C), and 3-D representation of automatic segmentation of muscle groups (FIG. 9D).

Comparison Between SCI and ND Volumes

Figure 10:
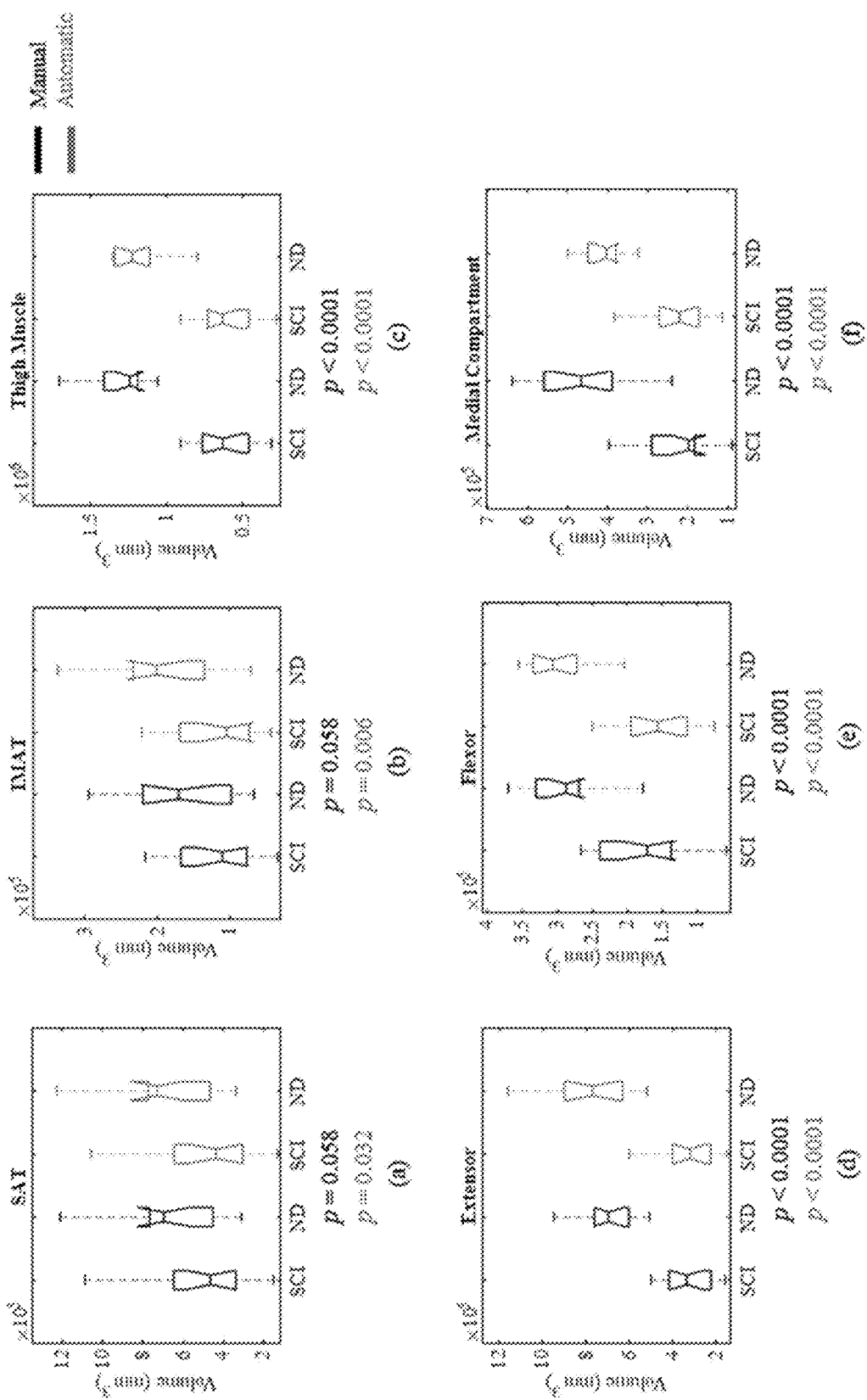
FIG. 10 depicts boxplot representations of calculated volumes and ratios for SCI and ND subjects as determined by manual (left) and automatic (right) segmentation results for (A) Extensor volume; (B) Flexor volume; (C) Medial volume; (D) IMAT volume; (E) SAT volume; (F) Total muscle volume; and (G) IMAT/muscle.

The volumes of SAT, IMAT, thigh muscle, extensor muscles, flexor muscles, and medial compartment muscles were calculated based on both manual and automatic segmentation for all subjects, and presented for the SCI and ND groups separately (FIG. 10). In order to determine any statistically significant difference between SCI and ND groups for each of these parameters, we used the non-parametric two-tailed Wilcoxon rank sum test with alpha level set at 0.05. This test can be used for two populations with unequal sample sizes and independent samples. The SAT and IMAT volumes were significantly greater in ND compared to SCI when the results from automatic segmentation were considered (FIGS. 10A and 10B), and the same trend, close to statistical significance (p=0.058), was observed also for manual segmentation. All muscle-related volumes were significantly greater in the ND group (p<0.0001) when both manual and automatic segmentation were considered (FIGS. 10C to 10F).

Figure 11:
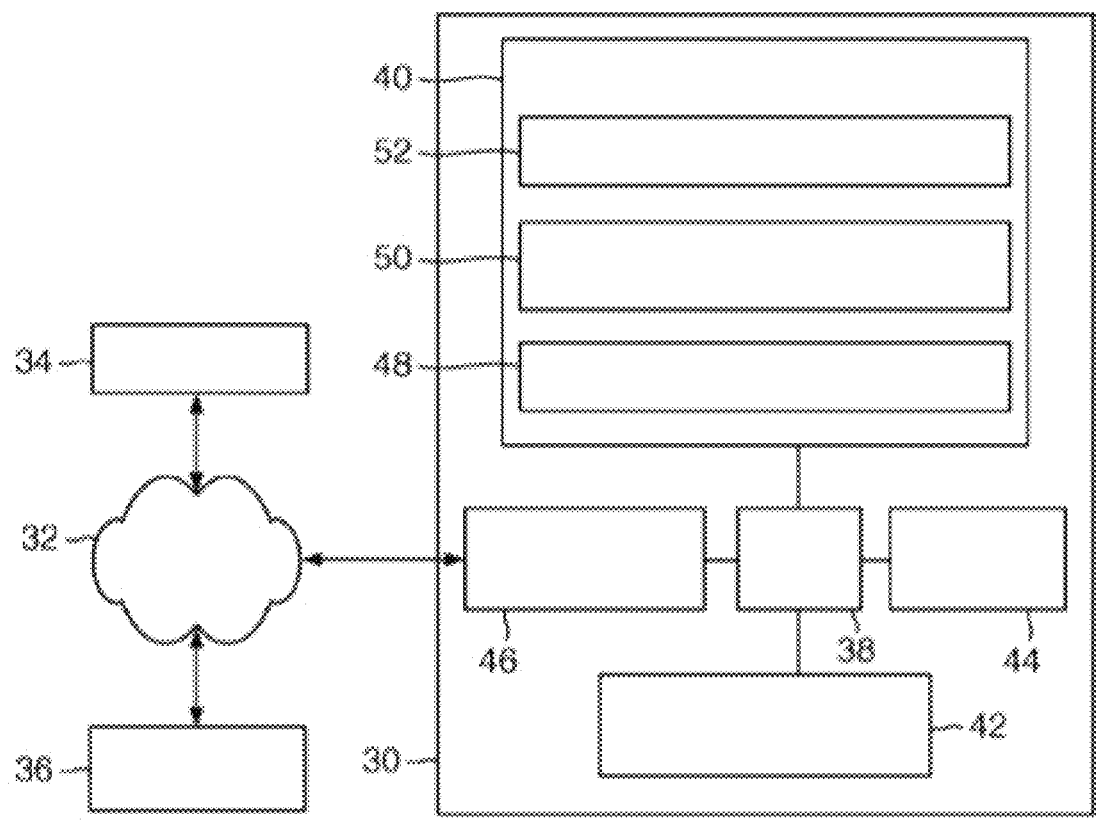
FIG. 11 is a block diagram of an exemplary apparatus suitable for implementing steps from the process of FIG. 1.

One or more steps in process 10 depicted in FIG. 1 may be implemented in an automated fashion, utilizing a computer or other electronic device to implement such steps. FIG. 11, for example, illustrates an exemplary apparatus 30 within which various steps from process 10 may be implemented in a manner consistent with the invention. Apparatus 30 in the illustrated embodiment is implemented as a server or multi-user computer that is coupled via a network 32 to one or more client computers 34, as well as an imaging system 36, e.g., a magnetic resonance imaging device, etc. For the purposes of the invention, each computer 30, 34 may represent practically any type of computer, computer system, data processing system or other programmable electronic device. Moreover, each computer 30, 34 may be implemented using one or more networked computers, e.g., in a cluster or other distributed computing system. In the alternative, computer 30 may be implemented within a single computer or other programmable electronic device, e.g., a desktop computer, a laptop computer, a handheld computer, a cell phone, a set top box, etc.

Computer 30 typically includes a central processing unit 38 including at least one microprocessor coupled to a memory 40, which may represent the random access memory (RAM) devices comprising the main storage of computer 30, as well as any supplemental levels of memory, e.g., cache memories, non-volatile or backup memories (e.g., programmable or flash memories), read-only memories, etc. In addition, memory 40 may be considered to include memory storage physically located elsewhere in computer 30, e.g., any cache memory in a processor in CPU 38, as well as any storage capacity used as a virtual memory, e.g., as stored on a mass storage device 42 or on another computer coupled to computer 30. Computer 30 also typically receives a number of inputs and outputs for communicating information externally. For interface with a user or operator, computer 30 typically includes a user interface 44 incorporating one or more user input devices (e.g., a keyboard, a mouse, a trackball, a joystick, a touchpad, and/or a microphone, among others) and a display (e.g., a CRT monitor, an LCD display panel, and/or a speaker, among others). Otherwise, user input may be received via another computer or terminal.

For additional storage, computer 30 may also include one or more mass storage devices 42, e.g., a floppy or other removable disk drive, a hard disk drive, a direct access storage device (DASD), an optical drive (e.g., a CD drive, a DVD drive, etc.), and/or a tape drive, among others. Furthermore, computer 30 may include an interface 46 with one or more networks 32 (e.g., a LAN, a WAN, a wireless network, and/or the Internet, among others) to permit the communication of information with other computers and electronic devices. It should be appreciated that computer 30 typically includes suitable analog and/or digital interfaces between CPU 36 and each of components 40, 42, 44 and 46 as is well known in the art. Other hardware environments are contemplated within the context of the invention.

Computer 30 operates under the control of an operating system 48 and executes or otherwise relies upon various computer software applications, components, programs, objects, modules, data structures, etc., as will be described in greater detail below. Moreover, various applications, components, programs, objects, modules, etc. may also execute on one or more processors in another computer coupled to computer 30 via network 32, e.g., in a distributed or client-server computing environment, whereby the processing required to implement the functions of a computer program may be allocated to multiple computers over a network.

As an example, computer 30 may include a software program 50 used to implement one or more of the steps described above in connection with process 10. For the purposes of implementing such steps, an image database 52, storing medical image scans, may be implemented in computer 30. It will be appreciated, however, that some steps in process 10 may be performed manually and with or without the use of computer 30.

Various aspects of different embodiments of the present disclosure are expressed in paragraphs X1, X2, and X3 as follows:

X1. One embodiment of the present disclosure includes a process-implemented method for segmentation of a medical image comprising receiving medical imaging data of a body part; determining a volume of the body part; segmenting the volume of the body part into at least muscle tissue volume and adipose tissue volume; and segmenting the muscle tissue volume into a plurality of different muscle group volumes.

X2. Another embodiment of the present disclosure includes a computer-implemented system for quantifying the effects of severe spinal cord injury, comprising at least one non-transitory computer readable storage medium having computer program instructions stored thereon; at least one processor configured to execute the computer program instructions causing the at least one processor to perform the following operations: receiving thigh scan images of a medical imaging scan of a thigh; determining a volume of the thigh; segmenting the volume of the thigh into at least muscle tissue volume and adipose tissue volume; and segmenting the muscle tissue volume into a plurality of different muscle group volumes.

X3. A further embodiment of the present disclosure includes a non-transitory computer readable storage medium having computer program instructions stored thereon that, when executed by a processor, cause the processor to perform the following operations: receiving medical imaging data of a body part; determining a volume of the body part; segmenting the volume of the body part into at least muscle tissue volume and adipose tissue volume; and segmenting the muscle tissue volume into a plurality of different muscle group volumes.

Yet other embodiments include the features described in any of the previous paragraphs X1, X2, or X3, as combined with one of more of the following aspects:

Wherein segmenting the muscle tissue volume into the plurality of different muscle group volumes comprises generating shape model of the muscle tissue volume; generating a second order model of the muscle tissue volume; generating a first order model of the muscle tissue volume; and segmenting the muscle tissue volume into the plurality of different muscle group volumes based at least in part on the spatial model, the first order model, and the second order model.

Wherein segmenting the volume of the body part into at least muscle tissue volume and adipose tissue volume includes segmenting the adipose tissue into a plurality of adipose tissues.

Wherein segmenting the adipose tissue into a plurality of adipose tissues includes segmenting the adipose tissues into subcutaneous adipose tissue and inter-muscular adipose tissue.

Wherein generating the shape model comprises selecting a training set of medical imaging scans of the body part, wherein, in each medical imaging scan in the training set, muscle tissue has been segmented into a plurality of muscle tissues; and registering the muscle tissue volume to training set already segmented into the plurality of muscle tissues to generate the shape model.

Wherein the medical imaging data includes a plurality of voxels, and wherein generating the first order model comprises generating a probability that a given voxel in the plurality of voxels is one of a plurality of muscle tissues.

Wherein generating the second order model comprises estimating pair-wise interactions between neighboring voxels in the medical imaging data.

Wherein the medical imaging data is generated using at least two different imaging modalities.

Wherein the at least two different imaging modalities include FS-MRI and WS-MRI.

Wherein segmenting the volume of the body part comprises applying linear combinations of discrete Gaussians to determine the threshold for each gray volume in the medical imaging data that extracts the adipose tissue and muscle tissue from background based at least in part on the at least two different imaging modalities.

Wherein generating the shape model comprises selecting a training set of thigh scan images, wherein, in each thigh scan image in the training set, muscle tissue has been segmented into a plurality of muscle tissues; and registering the muscle tissue volume to training set already segmented into the plurality of muscle tissues to generate the shape model.

Wherein each of the thigh scan images includes a plurality of voxels, and wherein generating the first order model comprises generating a probability that a given voxel in the plurality of voxels is one of a plurality of muscle tissues.

Wherein generating the second order model comprises estimating pair-wise interactions between neighboring voxels in the thigh scan images.

Wherein the medical imaging scan is generated using at least two different imaging modalities.

Wherein segmenting the volume of the thigh comprises applying linear combinations of discrete Gaussians to determine the threshold for each gray volume in the thigh scan images that extracts the adipose tissue and muscle tissue from background based at least in part on the at least two different imaging modalities.

The foregoing detailed description is given primarily for clearness of understanding and no unnecessary limitations are to be understood therefrom, for modifications can be made by those skilled in the art upon reading this disclosure and may be made without departing from the spirit of the invention. While the disclosed invention has been described primarily in connection with segmentation of human thigh muscles and adipose tissue in individuals with spinal cord injury, it should be understood that the segmentation techniques may be useable with healthy individuals, individuals with ailments apart from SCI, tissues other than thighs, and non-human patients.

What is claimed is:

1. A method for segmentation of a medical image comprising:
   receiving medical imaging data of a body part;
   determining a volume of the body part;
   segmenting the volume of the body part into at least muscle tissue; and
   segmenting the muscle tissue volume within the body part into a plurality of different muscle group volumes.

2. The method of claim 1, wherein segmenting the muscle tissue volume into the plurality of different muscle group volumes comprises:
   generating shape model of the muscle tissue volume;
   generating a spatial interaction model of the muscle tissue volume
   generating an intensity model of the muscle tissue volume; and
   segmenting the muscle tissue volume into the plurality of different muscle group volumes based at least in part on the shape model, the spatial interaction model, and the intensity model.

3. The method of claim 2, wherein generating the shape model comprises:
   selecting a training set of medical imaging scans of the body part, wherein, in each medical imaging scan in the training set, muscle tissue has been segmented into a plurality of muscle tissues; and
   registering the muscle tissue volume to the training set to generate the shape model.

4. The method of claim 2, wherein the medical imaging data includes a plurality of voxels, and wherein generating the intensity model comprises generating a probability that a given voxel in the plurality of voxels is one of a plurality of muscle tissues.

5. The method of claim 2, wherein generating the spatial interaction model comprises estimating pair-wise interactions between neighboring voxels in the medical imaging data.

6. The method of claim 1, wherein the medical imaging data is generated using at least two different imaging modalities; and wherein segmenting the volume of the body part comprises applying linear combinations of discrete Gaussians to determine the threshold for each gray volume in body part images in the medical imaging data that extracts the muscle tissue from background based at least in part on the at least two different imaging modalities.

7. The method of claim 1, wherein segmenting the volume of the body part into at least muscle tissue volume includes segmenting the volume of the body part into at least muscle tissue volume and adipose tissue volume.

8. A computer-implemented system for quantifying the effects of severe spinal cord injury, comprising:
   at least one non-transitory computer readable storage medium having computer program instructions stored thereon; and
   at least one processor configured to execute the computer program instructions causing the at least one processor to perform the following operations:
   receiving body part scan images of a medical imaging scan of a body part-thigh;
   determining a volume of the body part;
   segmenting the volume of the body part into at least muscle tissue volume; and
   segmenting the muscle tissue volume of the body part into a plurality of different muscle group volumes.

9. The computer-implemented system of claim 8, wherein segmenting the muscle tissue volume into the plurality of different muscle group volumes comprises:
   generating shape model of the muscle tissue volume;
   generating a spatial interaction model of the muscle tissue volume generating an intensity model of the muscle tissue volume; and segmenting the muscle tissue volume into the plurality of different muscle group volumes based at least in part on the shape model, the spatial interaction model, and the intensity model.

10. The computer-implemented system of claim 9, wherein generating the shape model comprises:
selecting a training set of body part scan images, wherein, in each body part scan image in the training set, muscle tissue has been segmented into a plurality of muscle tissues; and
registering the muscle tissue volume to the training set to generate the shape model.

11. The computer-implemented system of claim 9, wherein each of the body part scan images includes a plurality of voxels, and wherein generating the intensity model comprises generating a probability that a given voxel in the plurality of voxels is one of a plurality of muscle tissues.

12. The computer-implemented system of claim 9, wherein generating the spatial interaction model comprises estimating pair-wise interactions between neighboring voxels in the thigh scan images.

13. The computer-implemented system of claim 8, wherein the medical imaging scan is generated using at least two different imaging modalities; and
wherein segmenting the volume of the body part comprises applying linear combinations of discrete Gaussians to determine the threshold for each gray volume in the body part scan images that extracts the muscle tissue from background based at least in part on the at least two different imaging modalities.

14. The computer-implemented system of claim 8, wherein segmenting the volume of the body part into at least muscle tissue volume includes segmenting the volume of the body part into at least muscle tissue volume and adipose tissue volume.

15. A non-transitory computer readable storage medium having computer program instructions stored thereon that, when executed by a processor, cause the processor to perform the following operations:
receiving medical imaging data of a body part;
determining a volume of the body part;
segmenting the volume of the body part into at least muscle tissue volume; and
segmenting the muscle tissue volume within the body part into a plurality of different muscle group volumes.

16. The non-transitory computer readable storage medium of claim 15, wherein segmenting the muscle tissue volume into the plurality of different muscle group volumes comprises:
generating shape model of the muscle tissue volume;
generating a spatial interaction model of the muscle tissue volume
generating an intensity model of the muscle tissue volume; and
segmenting the muscle tissue volume into the plurality of different muscle group volumes based at least in part on the shape model, the intensity model, and the spatial interaction model.

17. The non-transitory computer readable storage medium of claim 16, wherein generating the shape model comprises:
selecting a training set of medical imaging scans of the body part, wherein, in each medical imaging scan in the training set, muscle tissue has been segmented into a plurality of muscle tissues; and
registering the muscle tissue volume to training set already segmented into the plurality of muscle tissues to generate the shape model.

18. The non-transitory computer readable storage medium of claim 16, wherein the medical imaging data includes a plurality of voxels, and wherein generating the intensity model comprises generating a probability that a given voxel in the plurality of voxels is one of a plurality of muscle tissues.

19. The non-transitory computer readable storage medium of claim 16, wherein generating the spatial interaction model comprises estimating pair-wise interactions between neighboring voxels in the medical imaging data.

20. The non-transitory computer readable storage medium of claim 15, wherein the medical imaging data is generated using at least two different imaging modalities; and
wherein segmenting the volume of the body part comprises applying linear combinations of discrete Gaussians to determine the threshold for each gray volume in body part images in the medical imaging data that extracts the muscle tissue from background based at least in part on the at least two different imaging modalities.

21. The non-transitory computer readable storage medium of claim 15, wherein segmenting the volume of the body part into at least muscle tissue volume includes segmenting the volume of the body part into at least muscle tissue volume and adipose tissue volume.

* * * * *